United States Patent [19]

Kolstad

[11] Patent Number: 4,867,897
[45] Date of Patent: Sep. 19, 1989

[54] GERMICIDAL IODOPHOR COMPOSITION

[75] Inventor: Robert A. Kolstad, Mesquite, Tex.

[73] Assignee: MDT Corporation, Torrance, Calif.

[21] Appl. No.: 64,749

[22] Filed: Aug. 3, 1987

[51] Int. Cl.$^4$ ............................ C11D 1/29; C11D 3/48
[52] U.S. Cl. ..................................... 252/106; 252/551; 424/672
[58] Field of Search ................ 424/150; 252/106, 107, 252/551

[56] References Cited

U.S. PATENT DOCUMENTS

| | | | |
|---|---|---|---|
| 3,240,711 | 3/1966 | Wittwer | 252/106 |
| 3,650,966 | 3/1972 | Bakka | 252/106 |
| 4,206,204 | 6/1980 | Langford | 424/150 |
| 4,207,310 | 6/1980 | Langford | 424/150 |
| 4,271,149 | 6/1981 | Winicov et al. | 424/150 |

OTHER PUBLICATIONS

Blatt, et al, An Evaluation of the Iodophor Compounds as Surgical Germicides, *Surgery Gynecology & Obstetrics*, Dec. '61, 699–704.

Block, et al, *Disinfection, Sterilization and Preservation*, pp. 183–196, 1983.

Gershenfeld and Witlin, Iodine as an Antiseptic, *Annals New York Academy of Sciences*, 1950, pp. 172–182.

Official monographs, USP XX, pp. 380 & 407.

*Primary Examiner*—Paul Lieberman
*Assistant Examiner*—Kathleen Markowski
*Attorney, Agent, or Firm*—Trask, Britt & Rossa

[57] ABSTRACT

A germicidal composition capable of action as an antiseptic or as a disinfectant contains a solvent, iodine and an anionic surfactant, such as nonylphenoxy(ethyleneoxy)$_4$ethanol sulfate. An admixture with sodium lauryl sulfate is preferred. Said composition, when diluted with water, has a free iodine content greater than that of the iodophors. Methods of making and using the composition are also disclosed.

21 Claims, 1 Drawing Sheet

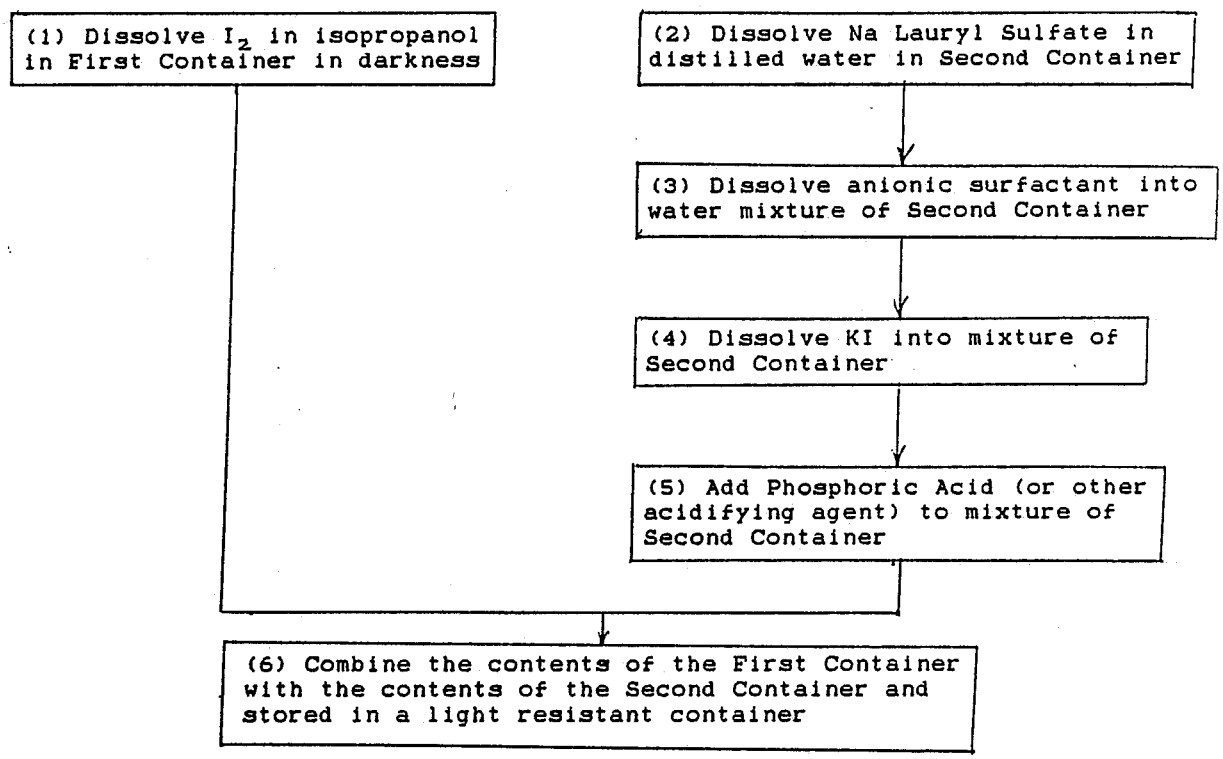
F I G. 1

GERMICIDAL IODOPHOR COMPOSITION

BACKGROUND OF THE INVENTION

1. Field

This invention relates to germicidal compositions generally, and to an anionic detergent and iodine commposition specifically.

2. State of the Art

For purposes of this disclosure, a disinfectant is a chemical applied to inanimate surfaces for the purpose of destroying microorganisms. An antiseptic is a chemical applied to living tissue for the purpose of preventing or arresting the growth of microscopic pathogens. Germicides incorporate the properties of both disinfectants and antiseptics.

Iodine's use in medicine dates back to at least 1830 when it was used as an antiseptic to treat wounds. Today, iodine is still recognized as a good general purpose antiseptic provided that appropriate dilutions of the compound are used. In addition, iodine is the active ingredient in numerous disinfectants.

Three classical iodine-containing formulations are Iodine Solution (USP), Strong Iodine Solution (USP), and Iodine Tincture (USP). Iodine Solution (USP) is understood to contain 1.8 to 2.2 grams (g) of iodine and 2.1 to 2.6 g of sodium iodide (NaI) in each 100 milliliters (ml) of water. Strong Iodine Solution (USP) (e.g. Lugol's Solution), contains 4.5 to 5.5g of iodine, and 9.5 to 10.5 g of potassium iodide (KI) in each 100 ml of water. Iodine Tincture (USP) preparations typically contain 1.8 to 2.2 g of iodine, and 2.1 to 2.6 g of NaI in a 100 ml solution of water and alcohol (50% by volume). All three of these preparations are effective as antiseptics, but are also highly toxic and bad smelling.

Iodine, although a good antiseptic, does have some drawbacks in high concentrations. It smells unpleasant, stains the skin a yellowish-brown, stains starch-containing materials blue, is unstable in solution, and can irritate or burn animal tissue.

As a disinfectant, iodine by itself has a limited ability to kill spores and may react chemically with metals and other materials, causing erosion.

To overcome some of the drawbacks associated with the use of iodine solutions as antiseptics, the iodophors were developed. Iodophors are generally defined as complexes of iodine and nonionic or cationic detergents which release iodine in water. Typical detergents used in compounding antiseptic iodophors are polyvinyl pyrrolidone, polyether glycols, polyvinyl alcohols, polyacrylic acids, polyamides, and polyoxy alkylenes.

Exemplary of the antiseptic iodophors is "PVP-iodine" or "povidone iodine" (Betadine ® by Purdue-Frederick). Povidone iodine contains polymeric polyvinyl pyrrolidone. When povidone iodine is diluted with water, free iodine releases into the solute.

Povidone iodine, like the other iodophors, has the unusual characteristic of having a specific dilution ratio (the "use-dilution") at which a maximum concentration of free iodine will be present in solution. "Free iodine," as used in this disclosure, is the concentration of the nonionic, antimicrobial species $I_2$ and HOI. L. Gershenfeld, et al., *Iodine as An Antiseptic*, Annals New York Academy of Sciences, 53:172-182 (1950). Mixing an iodophor with less water than that used with the use-dilution results in a decreased concentration of free iodine. Povidone iodine has a maximum attainable free iodine concentration of 25.6 ppm, which concentration is attainable at povidone iodine's use-dilution. S. Block, *Disinfection, Sterilization, and Preservation*, 183-196, 1983.

"Use-dilution" is not to be confused with "dilution of use." Dilution of use, as used in this disclosure, means the dilution or concentration at which the particular germicidal composition is used for whatever reason. The dilution of use need not necessarily be the dilution at which the maximal concentration of free iodine would be present.

The iodophors are benign to living tissue and lack the pungent odor characteristic of iodine containing solutions. These characteristics of the iodophors render them preferable to strong solutions of iodine (e.g., the three aforementioned USP preparations). R. Blatt et al., *An Evaluation of the Iodophor Compounds as Surgical Germicides*, J. Surgery, Gynecology and Obstetrics, 113:699-704 (1961).

The advantages gained by using the iodophors are offset to some extent by some disadvantages. Since each iodophor has a self-limiting maximum concentration of free iodine, and free iodine is the active germicidal agent, L. Gershenfeld, et al., *Iodine as An Antiseptic*, Annals New York Academy of Sciences, 53:172-182 (1950), more time is required for the iodophors to disinfect a treated area when compared with the aforementioned iodine solutions. For example, Wescodyne ®, a well known disinfectant, has a maximum free iodine concentration of 20 milligrams/liter (mg/l) at its use-dilution and requires a contact time of ten minutes to fulfill the criteria of an intermediate-level disinfectant (Environmental Protection Agency/Center for Disease Control standards).

A ten minute contact time can be excessive for busy medical or dental practices. Conditions in medical and dental offices, as well as emergency rooms, require successive patients to be treated at the same work station. The work station must be disinfected between each patient. Preoperative and postoperative disinfection are other common uses of the iodophors where a decreased treatment time would be useful.

Work has been done using undecoylium chloride-iodine, a complex of acycloaminoformylmethylpyridinium chloride and iodine. Undecoylium chloride-iodine has the activity of a cationic detergent and iodine's disinfectant action. This agent also has uses in preoperative and postoperative disinfection.

SUMMARY OF THE INVENTION

This invention comprises a germicidal composition in both concentrated and diluted forms, and a method of making and using the germicidal composition. The germicidal composition in its concentrated form comprises a liquid solvent; iodine in admixture with the liquid solvent; and an anionic surfactant in admixture with both the liquid solvent and the iodine. The iodine and the anionic surfactants are present in such quantities that when the germicidal composition is diluted with water to the dilution of use for the particular composition (i.e., the diluted form), free iodine is present in the resulting solution at a concentration greater than that of the iodophors (e.g. of 40 mg/l). A nonionic detergent may also be added to the composition. In a preferred embodiment, an acidifying agent is added to the composition, so that at the dilution of use, the pH is lowered to below about 6.5, extending the antimicrobial efficacy to approximately four weeks. A preferred liquid solvent is isopropanol. The composition usually contains potassium iodide (KI) or sodium iodide (NaI) to enhance the solubility of the iodine. A second anionic surfactant is preferably added to the composition to decrease "beading" and staining.

The concentrated composition can be made by dissolving iodine ($I_2$) into a liquid solvent. In a separate container, a surfactant is dissolved into another liquid solvent to form a second solution. An anionic surfactant is added to the second solution. A salt of iodine may be added to the second solution. An acidifying agent may be added to the second solution. The two separate solutions are combined, making the concentrate. The resulting concentrate is stored in a light-resistant container until use.

Upon use, the resulting solution is diluted with a particular amount of water to the particular composition's dilution of use. The dilution of use is chosen by the particular user.

DESCRIPTION OF THE DRAWINGS

The drawing is a flow chart outlining the steps one may use to compound the invention.

DETAILED DESCRIPTION OF THE PREFERRED EMBODIMENTS

The concentrated form of the germicidal composition of the present invention comprises a liquid solvent in admixture with iodine, and an anionic surfactant. When the germicidal composition is diluted with water to its dilution of use, free iodine is present in solution at a concentration higher than is available in iodophors; typically at least about 40 mg/l.

The liquid solvent should be one in which iodine is readily soluble. The preferred solvents are those which do not react detrimentally with anionic detergents or iodine, and the ideal solvents also enhance iodine's activity against microscopic pathogens. Solvents in which iodine is soluble include chloroform, carbon disulfide, carbon tetrachloride, benzene, ethanol, isopropanol, other alcohols, ether, glycerin, propylene glycol, and mixtures thereof, with or without water.

Isopropyl alcohol (isopropanol) is an ideal solvent for use in the composition. Isopropanol does not react detrimentally with iodine and is readily available in very pure forms at relatively low prices.

Ethanol is another ideal solvent for use in the composition having attributes similar to those of isopropanol.

Iodine will usually be present in the composition in two chemical forms, the first of which is pure iodine ($I_2$). Pure iodine is only slightly soluble in pure water (1:3450 at 20° centigrade (C.)), but is freely soluble in aqueous solutions containing soluble iodides ($I^-_{(aq)}$) and in various organic solvents. Accordingly, preferred compositions of the invention contain a relatively water soluble form of iodine, usually either sodium or potassium iodide. The addition of these relatively soluble salts of iodine to an aqueous solution increases the presence of the iodide anion in solution, thereby increasing the concentration of free iodine in the diluted composition.

Free iodine in solution is antimicrobial, making the composition an effective germicide. Free iodine is thought to destroy microbes by "addition reactions" to N—H, S—H, phenolic, and C=C groups among proteins, nucleic acids, and fatty acids. Whatever the reason, the greater the concentration of free iodine in a composition, the faster the composition works in destroying microorganisms.

Dilution of use is that concentration of the iodine-containing compound in water at which the composition is used. Unlike the iodophors, the present composition has no "use-dilution" at which a maximum amount of free iodine will be present in solution.

The present invention incorporates iodine and detergents in such a manner that, upon aqueous dilution to the composition's dilution of use, the free iodine content of the diluted composition is greater than that of the iodophors. The present invention, however, unlike strong Iodine Solution (USP) or Iodine Tincture (USP), does not stain hard surfaces and is mild to the hands.

Anionic detergents are the preferred anionic surfactants. Anionic detergents are generally amphipathic cleansing agents having a large non-polar hydrocarbon end that is oil-soluble, and an anionic polar end that is water-soluble. The hydrophilic polar end usually consists of a carboxylate, sulfate, or sulfonate. Typical examples of anionic detergents are sodium lauryl sulfate, sodium dodecyl sulfate, potassium laurate, sodium dodecane sulfonate, and various nonylphenoxypolyethyleneoxy-ethanol sulfate derivatives.

The nonylphenoxypolyethyleneoxy ethanol sulfate derivatives, in conjunction with sodium lauryl sulfate, are the preferred anionic detergents in the invention. They are efficacious, relatively inexpensive, readily available, and suppress staining better than the composition compounded with other anionic surfactants. Nonylphenoxy(ethyleneoxy)$_4$ ethanol sulfate, sold under the trade designation Polystep B-1, has been shown to stain items the least, while still yielding ideal results. Compositions of nonylphenoxylpolyethylene ethanol sulfate having two, six, and eight parts of ethylene oxide to one part of nonylphenoxy ethanol sulfate also performs well (i.e., nonylphenoxy(ethyleneoxy)$_2$ ethanol sulfate, nonylphenoxy(ethyleneoxy)$_6$ ethanol sulfate, and nonylphenoxy(ethyleneoxy)$_8$ ethanol sulfate).

Another preferred anionic surfactant is sodium lauryl ethoxysulfate. The use of sodium lauryl ethoxysulfate as the anionic surfactant in the composition results in a composition having properties very similar to a composition which uses nonylphenoxy(ethyleneoxy)$_4$ ethanol sulfate as the anionic surfactant. Sodium lauryl ethoxysulfate is generally classified as a member of the alkyl ether sulfate group of surfactants.

A preferred embodiment of the composition contains sodium lauryl sulfate. The sodium lauryl sulfate decreases "beading," the tendency of the solution to conglomerate into drops or "beads" on a hydrophobic surface (e.g., metals). The sodium lauryl sulfate is thought to decrease surface tension allowing the diluted composition to spread across the surface to be treated.

A solvent, typically water, is added to the concentrated composition to make the diluted composition. In one embodiment of the invention hard water (i.e., water containing calcium and magnesium salts) may be used. The water may contain certain impurities so long as the impurities do not interfere with the function of the composition. The amount of water to be added depends on the particular embodiment's dilution of use. An embodiment's dilution of use can be readily determined by conventional procedures used by those skilled in the art to determine the concentration of free iodine present in solution.

Aqueous dilutions of iodine self-inactive unless the pH is lower than about 6. To prevent such inactivation, acidifying agents may be added to the composition. Acidifying agents useful in the present invention are chemical compounds which tend to lower the pH of the solution, but which do not react detrimentally with any necessary component of the composition. An ideal acidifying agent is 85% phosphoric acid ($H_3PO_{4(aq)}$). Other useful agents include sodium phosphate and sodium sulfate.

Nonionic surfactants may also be added to the composition. Examples of useful nonionic surfactants include polyethyleneglycol monooleate, polyethyleneglycol monolaurate, coconut oil alkanolamide, and coconut fatty acid alkanolamide.

Care must be used in selecting a nonionic or anionic surfactant, or any other component of the composition, to ensure that no chemical or physical incompatibilities arise (e.g., mixing a cationic surfactant with an anionic surfactant). Well established principles of selection and formulation are fully applicable in the practice of this invention. Accordingly, those skilled in the art will experience no difficulty in selecting compatible components for a formulation of this invention.

The following examples further illustrate the invention.

EXAMPLE 1

| Component | Weight (g) | Proportion (%) |
|---|---|---|
| Iodine | 20 | 4.34 |
| Isopropanol (99%) | 156.16 | 33.88 |
| Sodium lauryl sulfate | 4 | 0.87 |
| Nonylphenoxy(ethyleneoxy)4 ethanol sulfate | 8 | 1.74 |
| Water, distilled | 200 | 43.39 |
| Potassium iodide | 12 | 2.60 |
| Phosphoric acid (85%) | 60.80 | 13.18 |
| TOTAL | 460.96 g | 100% |

The preparation of Example 1 has a typical dilution of use of one part to 214 parts of water and at that dilution yields 43 mg/l of free iodine. At its dilution of use, this preferred embodiment does not stain light-colored hard surfaces and is mild to the hands.

If a nonionic surfactant is to be added to the composition of Example 1, it should be added after the compounding of the listed components.

EXAMPLE 2

One and a half milliliters of the concentrated germicidal composition of Example 1 was diluted with 213.5 ml of water. At this dilution of use (3:425), approximately 65 mg/l of free iodine was present in solution.

EXAMPLE 3

The germicidal composition of Example 1 at the 1:214 dilution of use was studied to determine its effectiveness as a surface disinfectant against *Psuedomonas aeruginosas*, *Staphylococcus aureus*, and *Salmonella cholerasius*. The studies were accomplished by exposing contaminated cylinders to the composition for five minutes. For each bacterial species tested, sixty carriers were tested with each of three lots of the disinfectant. The procedures used were as described by the Association of Official Analytical Chemists. Killing was achieved in 60 of 60 replicates at five minute exposures in all three batches for both *S. aureus* and *S. cholerasius*. Killing was achieved in 59 of 60 replicates at five minute exposure in all three batches for *P. aeruginosa*, which represents a 95% confidence level.

As a general rule, concentrated solutions of iodine dissolved in either alcohol or an alcohol-water mixture are compatible with nonionic detergents, but form a precipitate with anionic detergents. Concentrated solutions of iodine dissolved in either alcohol or an alcohol-water mixture also containing nonionic detergents are stable upon dilution with distilled water, but form a precipitate when diluted with "hard" water (i.e., water having calcium and magnesium salts present).

Numerous stable dilutions can be prepared by adding concentrated iodine solution and concentrated detergents (nonionic, anionic, or mixtures of both) separately to hard water. In both the concentrated and diluted form of the invention, iodine and one of its salts (e.g., NaI or KI) dissolved in aqueous alcohol is compatible with anionic detergents, some nonionic detergents, or mixtures of both types.

EXAMPLE 4

| Component | Weight (g) | Proportion (%) |
|---|---|---|
| Iodine | 20 | 4.34 |
| Isopropanol (99%) | 156.16 | 33.88 |
| Sodium lauryl sulfate | 4 | 0.87 |
| Sodium lauryl ethoxysulfate | 8 | 1.74 |
| Water, distilled | 200 | 43.39 |
| Potassium iodide | 12 | 2.60 |
| Phosphoric acid (85%) | 60.80 | 13.18 |
| TOTAL | 460.96 g | 100% |

The preparation of Example 5 has a typical dilution of use of one and one half parts to 213.5 parts of water and at that dilution yields 64 mg/l of free iodine.

EXAMPLE 5

As shown in FIG. 1, the composition disclosed in Example 1 is compounded into the invention according to the following recipe: (1) The iodine is dissolved into the isopropanol (99%) in darkness in a first container. In the alternative, the compounds may be mixed in light, but in an opaque or light-resistant container. (2) In a second container, the sodium lauryl sulfate is dissolved into the distilled water. (3) The Polystep B-1 (the nonylphenoxy(ethyleneoxy)4 ethanol sulfate) is added to the distilled water mixture contained within the second container. (4) The potassium iodide is added to the resulting mixture contained within the second container. (5) The phosphoric acid is then added to the resulting mixture. Finally, the mixture of the second container is combined with the isopropanol-iodine mixture of the first container, and the resulting solution is stored in a light resistant (e.g., amber) bottle. The resultant solution is the concentrated form of the invention, having a typical dilution of use of 214 parts of hard water to one part concentrate.

The composition is used by applying the diluted composition to the surface to be disinfected and allowing five minutes to pass before removal. Spray application, swabbing, and wiping are all effective means of applying the composition to a surface.

The term "disinfectant," as used in this disclosure, is a subjective term. A surface or an object is "disinfected" when one skilled in the art would consider the surface or object sufficiently free of virulent microorganisms to be safely used for its intended purpose. For example, a probe being used to examine the mouth of a healthy dental patient may be considered "disinfected" for that purpose even though it would not be considered "disinfected" for uses on an immuno-compromised individual undergoing open heart surgery. In any event, the term is used in the same sense with reference to the compositions of this invention, as it is with reference to the iodine compositions previously used as germicides, disinfectants or antiseptics.

The composition may also be used as an antiseptic, as it does not burn animal tissues, and does destroy microorganisms.

Reference herein to specific details of certain embodiments is not intended to restrict the scope of the appended claims.

I claim:

1. A germicidal composition having a dilution of use consisting essentially of:
   a liquid solvent for iodine;
   iodine in admixture with said liquid solvent; and
   an anionic surfactant in admixture with said liquid solvent and said iodine, said anionic surfactant comprising nonylphenoxypolyethyleneoxy ethanol sulfate, said iodine and said anionic surfactant being present in such concentrations that when said germicidal composition is diluted with water to its dilution of use, free iodine is present in said diluted composition at a concentration greater than that of an iodophor.

2. The germicidal composition of claim 1 wherein said liquid solvent for iodine comprises isopropyl alcohol.

3. The germicidal composition of claim 1 including sodium lauryl sulfate.

4. The germicidal composition of claim 3 wherein said anionic surfactant comprises nonylphenoxy(ethyleneoxy)$_4$ ethanol sulfate.

5. The germicidal composition of claim 4 including an acidifying agent present in an amount effective to adjust the pH of said composition to within the range of about 3 to about 6.

6. The germicidal composition of claim 5 wherein said acidifying agent is phosphoric acid.

7. The germicidal composition of claim 1 including sodium dodecyl sulfate.

8. The germicidal composition of claim 6 including a nonionic surfactant.

9. The germicidal composition of claim 1 wherein said anionic surfactant is nonylphenoxy(ethyleneoxy)$_2$ ethanol sulfate.

10. The germicidal composition of claim 1 wherein said anionic surfactant is nonylphenoxy(ethyleneoxy)$_6$ ethanol sulfate.

11. The germicidal composition of claim 1 wherein said anionic surfactant is nonylphenoxy(ethyleneoxy)$_8$ ethanol sulfate.

12. The germicidal composition of claim 1 wherein said liquid solvent for iodine comprises ethanol.

13. The germicidal composition of claim 5 including an acidifying agent present in an amount effective to adjust the pH of said composition to within the range of about 3 to about 6.

14. The germicidal composition of claim 13 wherein said acidifying agent is phosphoric acid.

15. A germicidal composition having a dilution of use comprising isopropanol, iodine in admixture with said isopropanol, and nonylphenoxy(ethyleneoxy)$_4$ ethanol sulfate in admixture with said isopropanol and said iodine, said iodine and said nonylphenoxyl(ethyleneoxy)$_4$ ethanol sulfate being present in such quantities than when said germicidal composition is diluted with water to a dilution of use, free iodine is present in said diluted solution at a concentration of at least 40 milligrams per liter.

16. The germicidal composition of claim 15 including an acidifying agent.

17. The composition of claim 16 wherein said acidifying agent is phosphoric acid.

18. The composition of claim 17 including sodium lauryl sulfate.

19. In iodine releasing germicidal compositions of the type having iodine, an anionic surfactant, and water, the improvement comprising selecting said anionic surfactant from the group consisting essentially of nonylphenoxypolyethyleneoxy ethanol sulfate and mixtures of an anionic detergent consisting essentially nonylphenoxypolyethyleneoxy ethanol sulfate and a nonionic detergent so that free iodine is present in the composition at a concentration of 40 milligrams per liter.

20. A method of disinfecting a surface comprising applying to said surface a germicidal composition comprising a liquid solvent for iodine, and anionic surfactant comprising nonylphenoxypolyethyleneoxy ethanol sulfate, free iodine and water, wherein said free iodine is present at a concentration of at least 40 milligrams per liter, and maintaining said germicidal composition in contact with said surface for a duration sufficient to disinfect said surface.

21. A method of making a germicidal composition comprising:
   dissolving iodine into a first solvent in a first container;
   dissolving an anionic detergent comprising nonylphenoxypolyethyleneoxy ethanol sulfate into a second solvent in a second container;
   dissolving a water soluble iodide into said second solvent in said second container, combining, in darkness, the contents of the first container with the contents of the second container, and diluting the combined solution with a predetermined quantity of water.

* * * * *